(12) United States Patent
Tanner et al.

(10) Patent No.: US 8,256,460 B2
(45) Date of Patent: Sep. 4, 2012

(54) DEVICE FOR CONTROLLED OPERATION OF A SURGICAL OR DENTAL DRIVE UNIT

(75) Inventors: Peter Tanner, Bubendorf (CH); Arthur Meili, Thürnen (CH)

(73) Assignee: Synthes USA, LLC, West Chester, PA (US)

( * ) Notice: Subject to any disclaimer, the term of this patent is extended or adjusted under 35 U.S.C. 154(b) by 1162 days.

(21) Appl. No.: 11/915,263

(22) PCT Filed: May 25, 2005

(86) PCT No.: PCT/CH2005/000294
§ 371 (c)(1),
(2), (4) Date: Mar. 24, 2008

(87) PCT Pub. No.: WO2006/125326
PCT Pub. Date: Nov. 30, 2006

(65) Prior Publication Data
US 2008/0190636 A1    Aug. 14, 2008

(51) Int. Cl.
*F16K 35/00* (2006.01)
(52) U.S. Cl. ........................ 137/614.19; 251/89; 251/295
(58) Field of Classification Search .................. 137/613, 137/614.19; 251/89, 111, 295; 604/128; 433/80, 84, 85, 133; 409/904; 200/86.5; 318/551; 74/512–514, 481; 173/168, 170; 239/526, 583
See application file for complete search history.

(56) References Cited

U.S. PATENT DOCUMENTS

| | | | |
|---|---|---|---|
| 3,136,059 A * | 6/1964 | Nelson | 433/127 |
| 3,590,813 A | 7/1971 | Roszyk | |
| 3,732,622 A * | 5/1973 | Rackson | 433/27 |
| 3,752,241 A | 8/1973 | Bent | |
| 3,989,952 A | 11/1976 | Hohmann et al. | |
| 4,106,750 A | 8/1978 | Karden et al. | |
| 4,221,359 A * | 9/1980 | Grimaldo | 251/295 |
| 4,523,911 A * | 6/1985 | Braetsch et al. | 433/101 |
| 5,515,930 A * | 5/1996 | Glaser | 173/115 |
| 5,697,158 A * | 12/1997 | Klinzing et al. | 30/166.3 |
| 6,032,922 A * | 3/2000 | Shew | 251/99 |

(Continued)

FOREIGN PATENT DOCUMENTS

CN 2444568 8/2001

(Continued)

*Primary Examiner* — Stephen M Hepperle
*Assistant Examiner* — Seth Faulb
(74) *Attorney, Agent, or Firm* — Fay Kaplun & Marcin, LLP

(57) ABSTRACT

A device for controlled operation of a surgical or dental drive unit driven by a compressed fluid source p available in the operating room and comprising A) a control valve attachable to the drive unit for controlling a flow rate of a compressed fluid flowing from a compressed fluid source p to a drive unit; B) a first control means by means of which the control valve is operable; and C) a second control means by means of which a flow rate of compressed fluid may be controlled. The device further comprises D) a control switch which is attached to the control valve and allowing to select between at least three positions (A;B;C): in position A the control valve is locked and closed; in position B the control valve is unlocked and a flow rate of the compressed fluid is controllable by means of the first control means; and in position C the control valve is unlocked and open permitting the control of a flow rate by means of the second control means.

11 Claims, 3 Drawing Sheets

U.S. PATENT DOCUMENTS

| | | | |
|---|---|---|---|
| 6,152,941 A * | 11/2000 | Himes et al. | 606/180 |
| 6,176,853 B1 * | 1/2001 | Stolyarenko | 606/1 |
| 6,247,929 B1 * | 6/2001 | Bachman et al. | 433/80 |
| 6,520,976 B1 * | 2/2003 | Gage | 606/170 |
| 2003/0181934 A1 * | 9/2003 | Johnston et al. | 606/167 |
| 2005/0001070 A1 * | 1/2005 | Wu | 239/526 |

FOREIGN PATENT DOCUMENTS

FR        1 246 545        11/1960

* cited by examiner

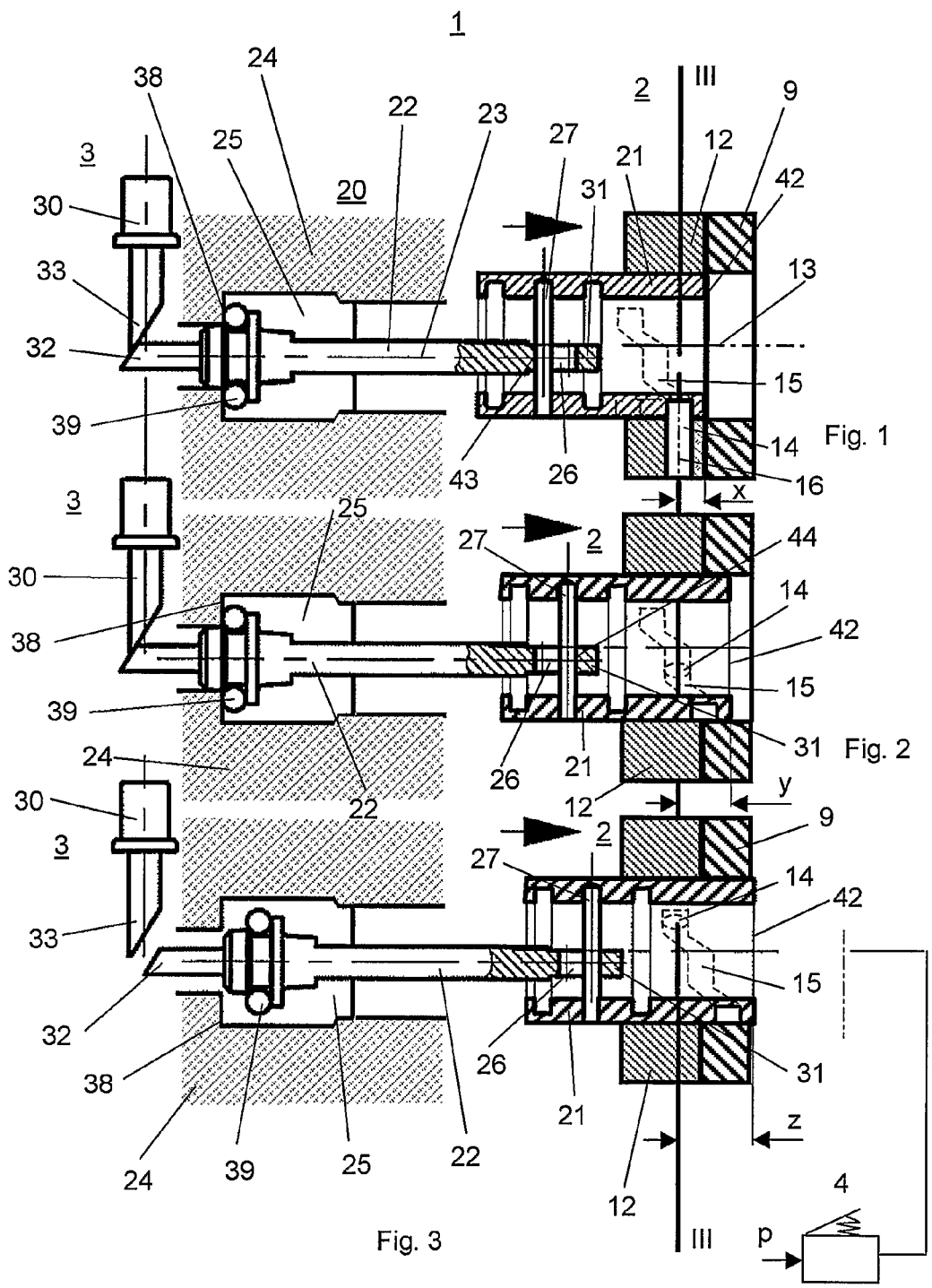

DEVICE FOR CONTROLLED OPERATION OF A SURGICAL OR DENTAL DRIVE UNIT

FIELD OF INVENTION

The invention relates to a device for controlled operation of a surgical or dental drive unit.

BACKGROUND INFORMATION

From U.S. Pat. No. 3,989,952 HOHMANN a dental apparatus is known which is provided with a plurality of instruments and electrically or pneumatically driven drive devices. Each drive device may be actuated by means of a foot controlled arrangement or alternatively by a hand controlled means. Furthermore, the dental apparatus has a support arrangement for the drive devices, so that upon withdrawal of a drive device from its support a switch is closed thus permitting actuation of the drive device. Once the drive device is withdrawn from its support it may be erroneously or unintentionally actuated.

SUMMARY OF INVENTION

The present invention relates to a device for controlled operation of a drive device that has an integrated main switch by means of which the drive is either put out of operation and locked or else a selection between an integrated first control means or a remote second control means is permitted.

The following are some of the advantages of the present invention:
- the operator may choose between an actuation of the drive unit by means of a first control means controlled by hand or a second control means controlled by hand, foot or by means of a computer;
- the operator does not have to avert his attention from the operating site since the control switch is attachable to the drive unit; and
- a secure operation is permitted since the control valve may be locked in its closed position thereby preventing an erroneous or unintended actuation of the drive unit.

In a preferred embodiment the control switch has a fourth position D in which the control valve may only be partially opened. This allows a restriction of the flow rate through the control valve to an allowable flow rate "r" which is smaller than the maximum flow rate "R". The restriction of the flow rate allows a limitation of the maximum rotational speed of the drive unit with regard to the chosen tool, e.g. drill bits with different diameters.

Preferably, the allowable flow rate "r" is in the range of 25% and 75% of the maximum flow rate "R".

In a further embodiment the control switch is configured to permit a continuous variation of the ratio r/R, therewith allowing a continuous variation of the rotational speed of a drive unit coupled to the device.

In another embodiment the control switch is configured to permit a stepwise variation of the ratio r/R.

In yet another embodiment the first control means comprise an operating means which is reversibly attachable to the device. This embodiment allows the advantage that the operator is not disturbed through the hand controlled operating means when the control of the drive unit is performed through the second control means, e.g. a control means being operated by foot or by a computer.

In a further embodiment the operating means is provided with a locking means for being reversibly locked. This embodiment allows the advantage that a drive unit coupled to the device may not be unintendetly actuated when the device together with the drive unit is laid down.

In yet a further the second means is actuable by foot. This embodiment allows the advantage that the drive unit may be alternatively operated by hand by means of the first control means when the control switch is in position B or by foot by means of the second control means when the control switch is in position C.

In another embodiment the control valve is open but put out of operation upon switching the control switch in its position C. This allows that advantage that the drive unit may be operated by means of a common control means actuated by foot.

In a further embodiment the control valve is provided with a valve body having a longitudinal axis, a control sleeve apt to lock or unlock the control valve and a valve piston being apt for the control of the flow rate of a compressed fluid.

In yet a further embodiment the valve piston is displaceable along the longitudinal axis by means of the first control means in order to control the flow rate of compressed fluid.

The invention and additional configurations of the invention are explained in even more detail with reference to the partially schematic illustration of several embodiments.

BRIEF DESCRIPTION OF DRAWINGS

The figures depict:

FIG. 1 a schematic view of an embodiment of the control valve according to the invention in its closed and locked position;

FIG. 2 a schematic view of the embodiment of the control valve shown in FIG. 1 in its unlocked position and being controllable by the first control means actuable by hand;

FIG. 3 a schematic view of the embodiment of the control valve shown in FIGS. 1 and 2 in its unlocked position and being controllable by means of a second control means actuated by foot;

DETAILED DESCRIPTION

Figure 4:
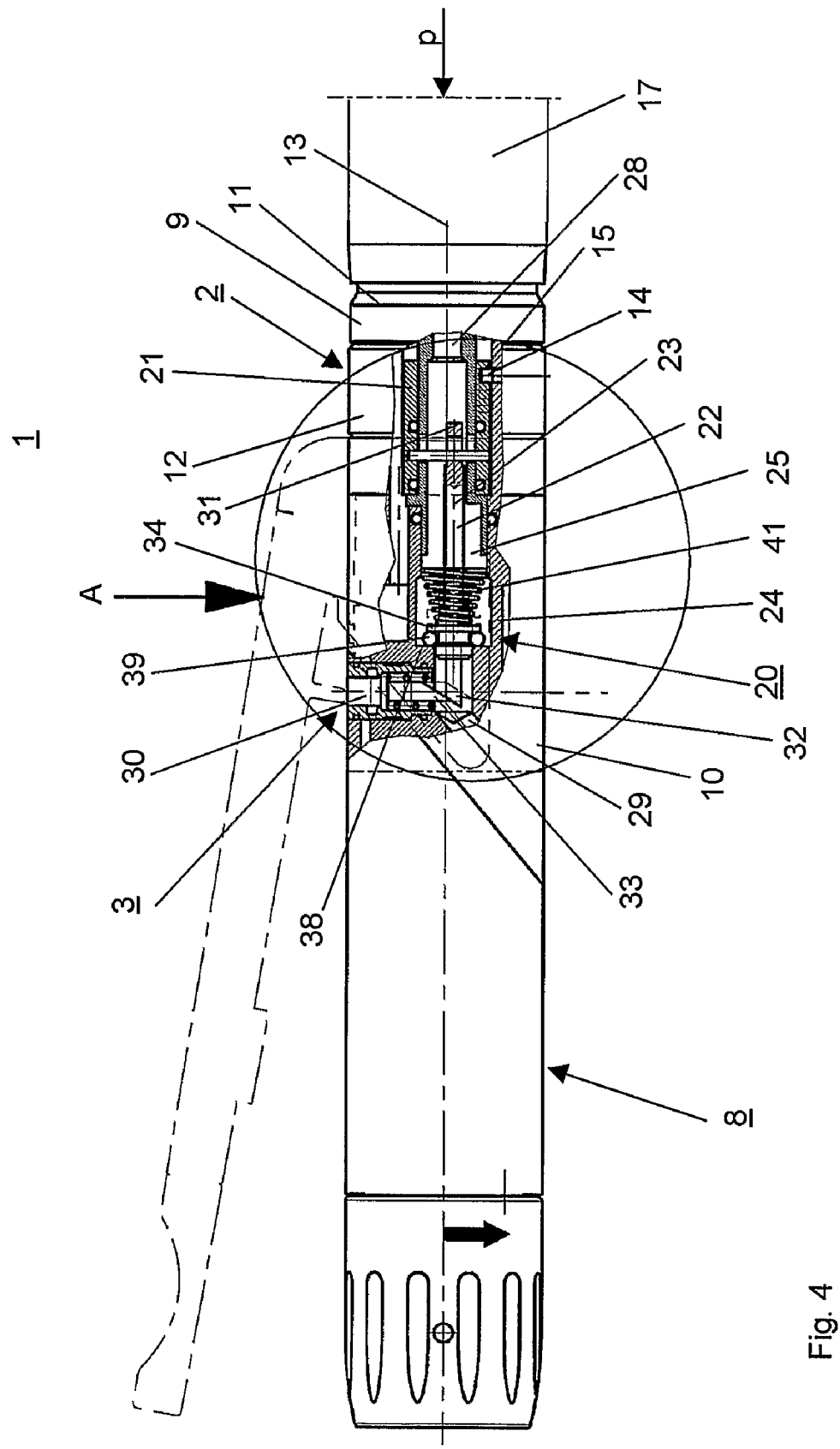
FIG. 4 a longitudinal section through a drive unit with an integrated embodiment of the device according to the invention.

FIGS. 1 to 3 schematically depict the control valve 20 with the ring member 12 of the control switch 2 (FIG. 4) being in position A (FIG. 1), in position B (FIG. 2) and in position C (FIG. 3). Upon rotating the ring member 12 around the central axis 13 of the device I (FIG. 4) the pin 14 slides along the peripheral axially stepped groove 15 at the control sleeve 21 while keeping its axial position on the line III-III such that the control sleeve 21 is axially displaced. The different axial positions of the control sleeve 21 permit firstly to lock (Position A) or unlock (Position B or C) the control valve 20. Therefore, the valve piston 22 comprises an oval aperture 26 arranged at its trailing end 31 and penetrating the valve piston 22 orthogonal to the longitudinal axis 23 of the valve piston 22. Furthermore, the control sleeve 21 is provided with a rod member 27 arranged diametrically and orthogonally to the longitudinal axis 23 of the valve piston 22 whereby the rod member 27 penetrates the oval aperture 26.

Upon switching the control switch 2 in its position A (FIG. 1) by axially displacing the control sleeve 21 to a distance x between the line III-III and the terminal end face 42 of the control sleeve 21 by means of rotating the ring member 12 the rod member 27 is also axially displaced until it contacts the wall of the oval aperture 26 at the first end 43 of the oval aperture 26 which is remote to the terminal end face 42. In this position of the control sleeve 21 the valve piston 22 is axially blocked. The oval aperture 26 is situated at the trailing end 31 of the valve piston 22 while the leading end 32 of the valve piston 22 is configured obliquely to the longitudinal axis 23, whereby said leading end 32 matches with the complementary oblique front piece 33 of the slide member 30. Since in position A the valve piston 22 is locked against displacement towards the rod member 27 the control valve 20 may not be actuated through the slide member 30.

In FIG. 2 the control switch 2 is shown in its position B in which the control sleeve 21 with the rod member 27 is axially displaced to a distance y>x between the line III-III and the terminal end face 42 of the control sleeve 21. The rod member 27 is now in contact with the wall of the oval aperture 26 at the second end 44 of the oval aperture 26 which is next to the terminal end face 42 of the control sleeve 21. Such the valve piston 22 may now be displaced parallel to its longitudinal axis 23 towards the rod member 27 by means of the first control means 3 therewith continuously opening or closing the control valve 20 at the valve face 38.

FIG. 3 depicts the control switch 2 in its position C in which the control sleeve 21 with the rod member 27 is axially displaced to a distance z>y between the line III-III and the terminal end face 42 of the control sleeve 21. Since the rod member 27 is in contact with the wall at the second end 44 of the oval aperture 26 the valve piston 22 is axially displaced towards the rear end 11 of the device 1 (FIG. 4) and the control valve 20 is opened at the valve face 38. The valve piston 22 is situated so far away from the slide member 30 that the slide member 30 is at a distance to the leading end 32 of the valve piston 22 such that the valve piston 22 may not be axially displaced through the displacement of the slide member 30. The control of the flow of a compressed fluid must now be effected by means of a second control means 4, e.g. an external control valve operated by foot connected to the adapter 9 and to a source of compressed fluid p available in the operating room.

FIG. 4 depicts an embodiment of the device 1 which is coaxially attached to a drive unit 8 with its front end 10 and which is provided with an adapter 9 for a flexible tube 17 for compressed fluid at its rear end 11. The flexible tube 17 is connectable e.g. to a source of compressed fluid p available in the operating room. The control valve 20 comprises a valve housing 24 with a central cavity 25, an inlet 28 adjacent to the adapter 9 for the compressed fluid and an outlet 29 connected to the drive unit 8. Furthermore, the control valve 12 comprises a valve piston 22 being displaceable in the cavity 25 along its longitudinal axis 23 and relative to the valve housing 24. Towards the front end 10 of the device 1 the valve piston 22 comprises a shoulder 34 concentrically arranged and having a valve seal 39 attached. Upon deactuating the control valve 20 the valve seal 39 is axially pressed against a valve face 38 at the valve housing 24 by means of a helical spring 41. Adjacent to the shoulder 34 the leading end 32 of the valve piston 22 is located which is obliquely shaped relative to longitudinal axis 23 of the valve piston 22. The oblique shaped leading end 32 of the valve piston 22 permits an axial displacement of the valve piston 22 against the force of the spring 41 by means of a slide member 30 being slideable perpendicularly to the longitudinal axis 23 of the valve piston 22 and having a complementarily shaped oblique front piece 33. In FIG. 1 the control switch 2 is in its position A such that the control valve 20 is locked and closed.

The control switch 2 comprises a control sleeve 21 being displaceable parallel to the longitudinal axis 23 and by means of which the control valve 20 may be put in one of its positions A;B;C i.e. locked and closed, unlocked and having the flow rate controlled by means of the first control means 3, or unlocked and open. The actuation of the control switch 2 is effected through a ring member 12 being arranged concentrically to the central axis 13 of the device 1 and being rotatable around the central axis 13 thus switching between the positions A;B;C. Upon rotating the ring member 12 from one position to another the control sleeve 21 is axially displaced by means of a pin 14 connected to the ring member 12 and engaging a groove 15 in the control sleeve 21 which extends on the outer periphery of the control sleeve 21 and which is axially stepwise configured (not shown) therewith allowing to axially displace the control sleeve 21.

Figure 5:
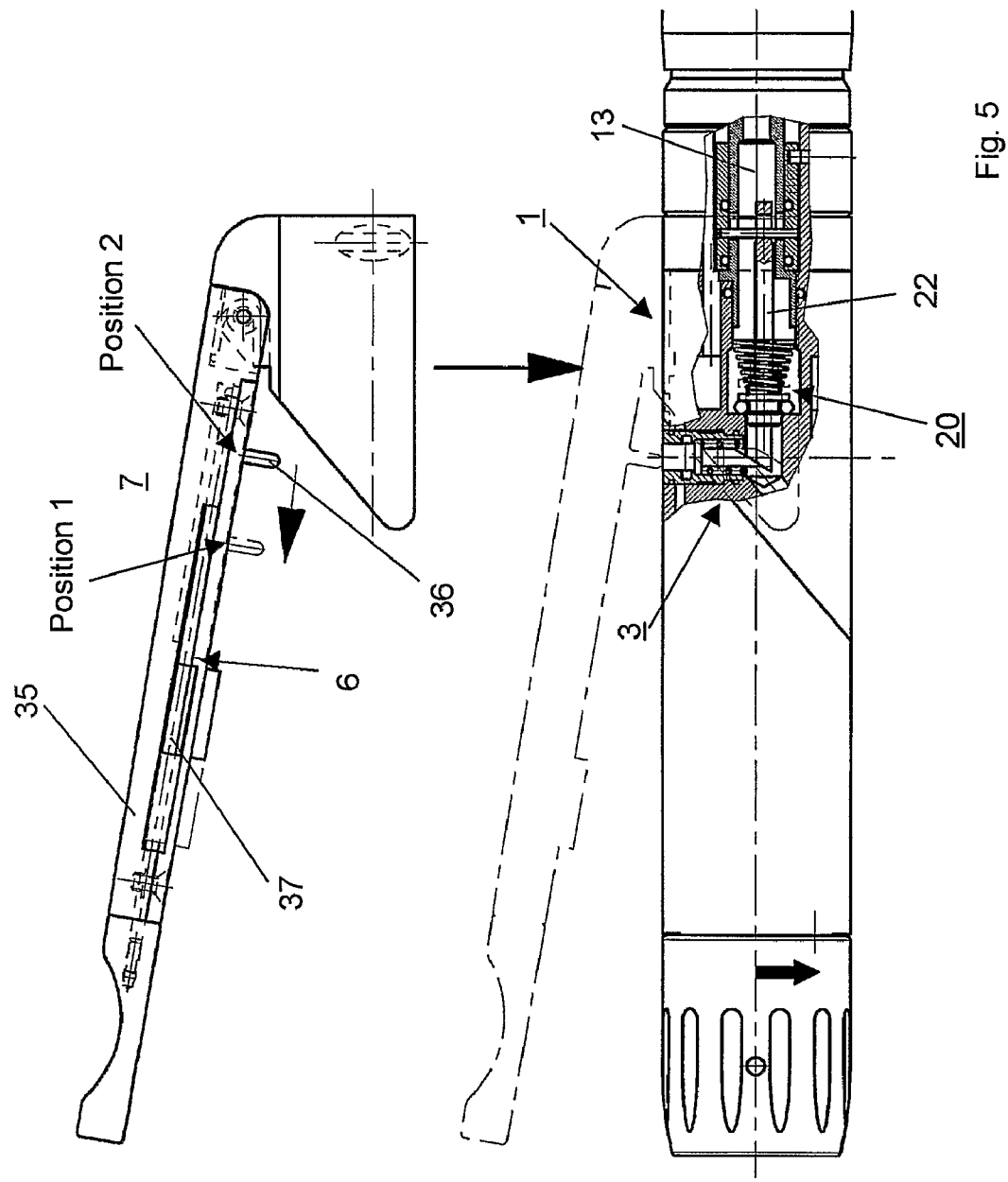
FIG. 5 a plane view of an embodiment of the device with an operating means for the first control means actuable by hand and having integrated locking means in the unlocked state.

FIG. 5 depicts an embodiment of operating means 7 actuable by hand which permits control of the first control means 3. The operating means 7 is reversibly mountable to the device 1. The operating means 7 comprises as a lever 35 being pivotably attached. The lever 35 includes a tappet 36 by means of which the slide member 30 may be pushed towards the leading end 32 of the valve piston 22 upon pivoting the lever 35 towards the central axis 13 of the device 1. Subsequently, the valve piston 22 is axially displaced thus permitting the control of the flow rate of compressed fluid through the control valve 20. Furthermore, the lever 35 includes a locking means 6 realised through a slide switch 37 by means of which the tappet 36 is moveable along the lever 35 in a first position 1 in which it may not contact the slide member 30 and in a second position 2 in which the tappet 36 may actuate the slide member 30.

The invention claimed is:

1. A device for controlled operation of a surgical or dental drive unit which is driven by a compressed fluid source, comprising:
    a control valve attached to a drive unit to control a flow rate of a compressed fluid flowing from a compressed fluid source to the drive unit;
    a first control arrangement controlling the control valve;
    a second control arrangement controlling the flow rate of the compressed fluid; and
    a control switch attached to the control valve and allowing to select between at least three positions, the at least three positions including a position A, a position B and a position C, wherein when the switch is in the position A, the control valve is locked and closed; when the switch is in the position B, the control valve is unlocked and the first control arrangement controlling the flow rate of the compressed fluid, and when the switch is in the position C, the control valve is unlocked and open so that the second control arrangement controls the flow rate of the compressed fluid, and the first control arrangement is incapable of controlling the control valve.

2. The device according to claim 1, wherein the at least three positions includes a position D and wherein when the switch is the position D, the control valve is only partially opened restricting the flow rate through the control valve to a predetermined flow rate, the predetermined flow rate being is smaller than a maximum flow rate.

3. The device according to claim 2, wherein the predetermined flow rate is in a range between 25% and 75% of the maximum flow rate.

4. The device according to claim 2, wherein the control switch permits a continuous variation of a ratio which is calculated as a function of the predetermined and maximum flow rates.

5. The device according to claim 2, wherein the control switch permits a stepwise variation of the ratio which is calculated as a function of the predetermined and maximum flow rates.

6. The device according to claim 1, wherein the first control arrangement includes a hand controllable operating arrangement which is reversibly attachable to the device.

7. The device according to claim 6, wherein the operating arrangement includes a locking arrangement for reversible locking.

8. The device according to claim 1, wherein the second control arrangement is actuable by foot.

9. The device according to claim 1, wherein, upon switching the control switch into the position C, the control valve switch from being open to being out of operation.

10. A device for controlled operation of a surgical or dental drive unit
which is driven by a compressed fluid source, comprising:
a control valve attached to a drive unit to control a flow rate of a compressed fluid flowing from a compressed fluid source to the drive unit;
a first control arrangement controlling the control valve;
a second control arrangement controlling the flow rate of the compressed fluid; and
a control switch attached to the control valve and allowing to select between at least three positions, the at least three positions including a position A, a position B and a position C, wherein when the switch is in the position A, the control valve is locked and closed; when the switch is in the position B, the control valve is unlocked and the first control arrangement controlling the flow rate of the compressed fluid, and when the switch is in the position C, the control valve is unlocked and open so that the second control arrangement controls the flow rate of the compressed fluid, wherein the control valve includes (a) a valve body having a longitudinal axis, (b) a control sleeve which one of locks and unlocks the control valve and (c) a valve piston controlling of the flow rate of the compressed fluid.

11. The device according to claim 10, wherein the valve piston is displaceable along the longitudinal axis using the first control arrangement in order to control the flow rate of the compressed fluid.

* * * * *